(12) United States Patent
Papenfuss

(10) Patent No.: US 10,492,800 B2
(45) Date of Patent: Dec. 3, 2019

(54) BONE CUTTING INSTRUMENT WITH EXPANDABLE SECTION

(71) Applicant: Lenkbar, LLC, Naples, FL (US)

(72) Inventor: Erik Papenfuss, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 388 days.

(21) Appl. No.: 15/357,373

(22) Filed: Nov. 21, 2016

(65) Prior Publication Data
US 2017/0143352 A1 May 25, 2017

Related U.S. Application Data

(60) Provisional application No. 62/259,847, filed on Nov. 25, 2015.

(51) Int. Cl.
*A61B 17/16* (2006.01)

(52) U.S. Cl.
CPC ................ *A61B 17/1617* (2013.01)

(58) Field of Classification Search
CPC . A61B 17/16; A61B 17/1613; A61B 17/1615; A61B 17/1617; A61B 17/1622; A61B 17/1624; A61B 17/1626; A61B 17/1628; A61B 17/1655; A61B 17/1657
USPC ..................................... 606/79, 80
See application file for complete search history.

(56) References Cited

U.S. PATENT DOCUMENTS

| | | | | |
|---|---|---|---|---|
| 3,827,821 A | * | 8/1974 | Swenson | B23B 51/102 408/159 |
| 4,475,852 A | * | 10/1984 | Koppelmann | B23B 51/102 408/159 |
| 5,443,475 A | * | 8/1995 | Auerbach | A61B 17/1608 600/564 |
| 5,445,639 A | * | 8/1995 | Kuslich | A61B 17/1671 606/180 |
| 6,740,090 B1 | * | 5/2004 | Cragg | A61B 17/1617 128/898 |
| 7,179,024 B2 | * | 2/2007 | Greenhalgh | B23B 51/0018 408/224 |
| 7,429,264 B2 | * | 9/2008 | Melkent | A61B 17/1617 606/159 |
| 7,828,804 B2 | * | 11/2010 | Li | A61B 17/1617 408/156 |

(Continued)

FOREIGN PATENT DOCUMENTS

WO        2014089198 A1    6/2014

OTHER PUBLICATIONS

International Preliminary Report on Patentability for International Application No. PCT/US2016/062026, dated May 22, 2018, 6 pages.

(Continued)

*Primary Examiner* — Eric S Gibson
(74) *Attorney, Agent, or Firm* — RatnerPrestia

(57) ABSTRACT

An instrument for cutting bone includes a hollow shaft having a sidewall. A cutting element is at least partially housed in the hollow shaft. The cutting element can include one or more cutting blades that are radially expandable through the sidewall. The instrument can also include a piercing tip on a distal end of the hollow shaft is located distally of the one or more cutting blades. In addition, the instrument can include an expansion element for radially expanding the one or more cutting blades through the sidewall.

25 Claims, 4 Drawing Sheets

(56) References Cited

U.S. PATENT DOCUMENTS

| | | | | |
|---|---|---|---|---|
| 8,246,627 | B2* | 8/2012 | Vanleeuwen | A61B 17/1617 606/79 |
| 8,343,158 | B2* | 1/2013 | Birkbeck | A61B 17/1617 606/80 |
| 8,888,781 | B2 | 11/2014 | Sterrett | |
| 9,364,259 | B2* | 6/2016 | Lunsford | A61B 17/320725 |
| 9,517,076 | B2* | 12/2016 | Papenfuss | A61B 17/1617 |
| 9,655,629 | B2* | 5/2017 | Takeuchi | A61B 17/1617 |
| 9,668,750 | B2* | 6/2017 | Mirochinik | A61B 17/1796 |
| 9,668,751 | B2* | 6/2017 | Papenfuss | A61B 17/1617 |
| 9,795,395 | B2* | 10/2017 | Lizardi | A61B 17/1622 |
| 2004/0208717 | A1* | 10/2004 | Greenhalgh | B23B 51/0018 408/224 |
| 2005/0096685 | A1 | 5/2005 | Murphy et al. | |
| 2005/0113836 | A1 | 5/2005 | Lozier et al. | |
| 2005/0277971 | A1* | 12/2005 | Melkent | A61B 17/1617 606/180 |
| 2006/0241629 | A1* | 10/2006 | Krebs | A61B 17/1617 606/80 |
| 2007/0123889 | A1* | 5/2007 | Malandain | A61B 17/1617 606/79 |
| 2007/0282345 | A1* | 12/2007 | Yedlicka | A61B 17/1615 606/80 |
| 2008/0114364 | A1* | 5/2008 | Goldin | A61B 17/1617 606/79 |
| 2008/0294168 | A1* | 11/2008 | Wieland | A61B 17/1617 606/80 |
| 2010/0094296 | A1* | 4/2010 | Birkbeck | A61B 17/1617 606/80 |
| 2010/0268175 | A1* | 10/2010 | Lunsford | A61B 17/320725 604/272 |
| 2011/0130760 | A1* | 6/2011 | Anderson | A61B 17/1617 606/79 |
| 2011/0251616 | A1* | 10/2011 | Osman | A61B 17/1671 606/80 |
| 2012/0022568 | A1 | 1/2012 | Koblish et al. | |
| 2013/0165935 | A1* | 6/2013 | Griffiths | A61B 17/1617 606/80 |
| 2013/0340240 | A1 | 12/2013 | Irawan | |
| 2014/0257297 | A1 | 9/2014 | Koogle et al. | |
| 2017/0143352 | A1* | 5/2017 | Papenfuss | A61B 17/1617 |

OTHER PUBLICATIONS

Australian Examination Report for Australian Application No. 2016355390, dated Sep. 24, 2018, 3 pages.

International Search Report and Written Opinion of the International Searching Authority for International Application No. PCT/US2016/062026, dated Jan. 27, 2017, 6 pages.

Extended European Search Report for European Application No. 16 866 945.5, dated May 22, 2019, 5 pages.

* cited by examiner

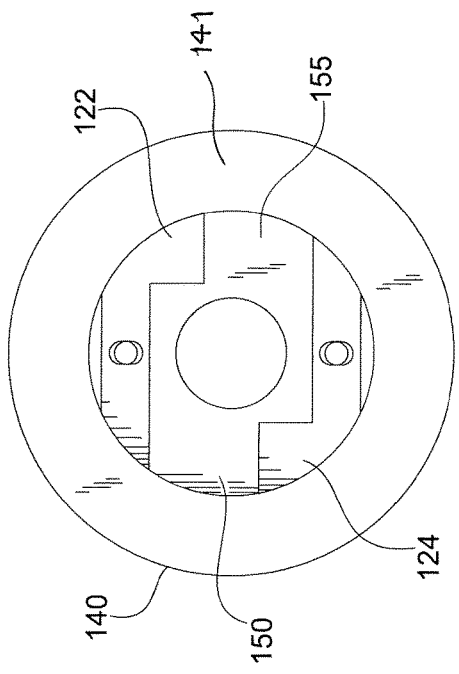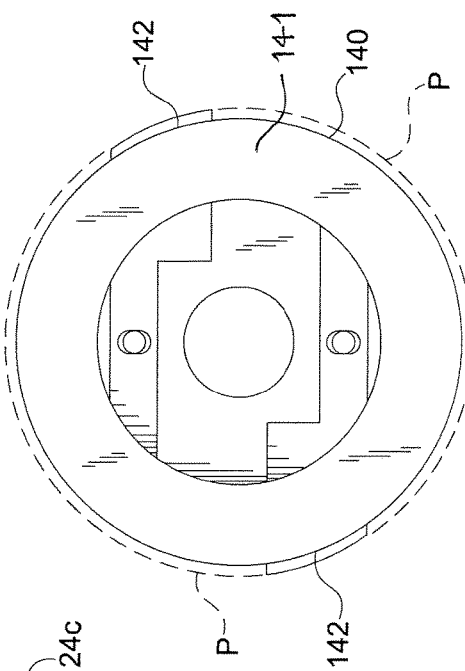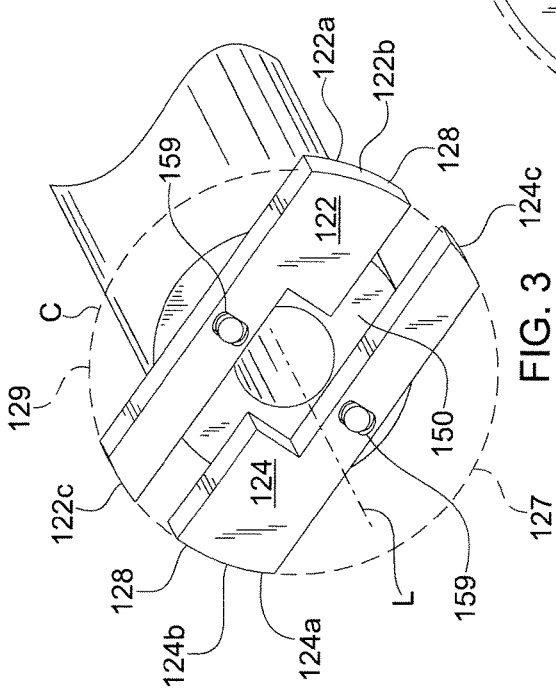

BONE CUTTING INSTRUMENT WITH EXPANDABLE SECTION

RELATED APPLICATION(S)

This application is related to and claims the benefit of priority under 35 U.S.C. § 119 of U.S. Provisional Application Ser. No. 62/259,847, filed Nov. 25, 2015, the content of which is incorporated by reference herein in its entirety.

FIELD

The present invention relates generally to surgical instruments for preparing pilot holes, tunnels, sockets and the like in bone, and more specifically to a surgical bone cutting instrument with one or more expandable elements that are selectively operable for preparing an enlarged hole section in bone.

BACKGROUND

Drilling and cutting instruments have been developed specifically for arthroscopic procedures. These instruments can be advanced through a small incision to a specific site, forming a tunnel in bone. A cutting blade on the instrument can be deployed within the tunnel to cut a socket or other enlarged diameter section, which can be used PCL reconstruction, ACL reconstruction or other procedures.

One drawback of conventional cutting instruments is that some instruments feature large projections, gaps and other discontinuities on the exterior surface of the instrument, particularly in the vicinity of the cutting blade. Large discontinuities on the exterior surface, particularly in the area of the cutting blade, can be undesirable because bone fragments and other debris can become lodged in those areas and interfere with the operation of the instrument.

U.S. Pat. No. 8,888,781 discloses a combined flip cutter and drill instrument. The instrument includes a cone shaped drill head that projects from the end of a hollow shaft. The drill head can be operated in a "straight" configuration, in which the drill head is parallel to the axis of the shaft, to drill a tunnel into bone. The drill head can also be pivoted approximately 90 degrees to a "flip" configuration, in which the drill head is disposed at an angle with respect to the shaft, to perform a bone cutting operation. To allow the drill head to pivot, the shaft has a large opening at the distal end of the shaft and openings in the sidewall of the shaft. As noted above, large openings in the exterior of a cutting instrument can cause an issue when bone fragments and debris become clogged in the openings.

The flip cutter in U.S. Pat. No. 8,888,781 is capable of retrograde cutting to create sockets or tunnels in bone. However, there is no indication that the flip cutter can cut bone in an anterograde manner. As such, it is unclear whether the flip cutter can cut sockets for every application.

SUMMARY

Instruments for tunneling and cutting in bone can be provided in various embodiments in accordance with the invention as will be described herein, any of which can be the subject of the claims.

In one beneficial embodiment of the invention, an instrument for cutting bone includes a hollow shaft having a sidewall. A cutting element can be at least partially housed in the hollow shaft. The cutting element can include one or more cutting blades that are radially expandable, relative to the longitudinal axis, through the sidewall. The instrument can also include a piercing tip on a distal end of the hollow shaft. The piercing tip can be located distally of the one or more cutting blades. The instrument can also include an expansion element for radially expanding the one or more cutting blades radially outwardly with respect to the longitudinal axis of the instrument and through the sidewall of the hollow shaft.

In the same embodiment, or in a different embodiment, the sidewall of the hollow shaft can define one or more apertures extending completely through the sidewall.

In the same embodiment, or in a different embodiment, the one or more apertures can be axially and radially aligned with the one or more cutting blades inside the hollow shaft.

In the same embodiment, or in a different embodiment, each of the one or more apertures can be closed on four sides within the sidewall of the hollow shaft.

In the same embodiment, or in a different embodiment, the expansion element can be an activation rod disposed inside the hollow shaft.

In the same embodiment, or in a different embodiment, the activation rod can include a distal end, the distal end having a distal end face.

In the same embodiment, or in a different embodiment, the one or more cutting blades can be mounted to the distal end face.

In the same embodiment, or in a different embodiment, the one or more cutting blades can be slidably coupled to the distal end face.

In the same embodiment, or in a different embodiment, the one or more cutting blades can be radially expandable, relative to the longitudinal axis, through the sidewall in response to rotation of the activation rod inside the hollow shaft.

In the same embodiment, or in a different embodiment, the activation rod can be rotatable relative to the hollow shaft between a first orientation, in which the one or more cutting blades are radially expanded through the one or more apertures to a cutting position, and a second orientation, in which the one or more cutting blades are radially retracted through the one or more apertures to a stowed position.

In the same embodiment, or in a different embodiment, the one or more cutting blades can be entirely contained within the perimeter of the hollow shaft when the activation rod is rotated to the second orientation.

In the same embodiment, or in a different embodiment, the one or more cutting elements can be coupled to a distal end of the activation rod.

In the same embodiment, or in a different embodiment, the one or more cutting elements can be pivotably mounted to the distal end of the activation rod.

In the same embodiment, or in a different embodiment, the one or more cutting elements can be slidably coupled to the distal end of the activation rod.

In the same embodiment, or in a different embodiment, the activation rod can include a cam mechanism for radially expanding the one or more cutting elements.

In the same embodiment, or in a different embodiment, the cam mechanism can include one or more pins extending longitudinally from the distal end of the activation rod.

In the same embodiment, or in a different embodiment, the one or more cutting elements can be mounted on the one or more pins to mount the one or more cutting elements to the distal end of the activation rod.

In the same embodiment, or in a different embodiment, the piercing tip can include a trocar tip.

In the same embodiment, or in a different embodiment, the trocar tip can be either a blunt tip or a sharp tip.

In the same embodiment, or in a different embodiment, the piercing tip can be a drill bit.

BRIEF DESCRIPTION OF THE DRAWINGS

The foregoing summary and the following detailed description will be better understood in conjunction with the non-limiting examples shown in the accompanying drawings, which are not to scale, of which:

FIG. 3 is a truncated perspective view of components of the bone tunneling instrument of FIG. 1;

FIG. 4 is an end view of the bone tunneling instrument of FIG. 1, with components shown in one mode of operation;

FIG. 5 is an end view of the bone tunneling instrument of FIG. 1, with components shown in another mode of operation.

DETAILED DESCRIPTION

Figure 1:
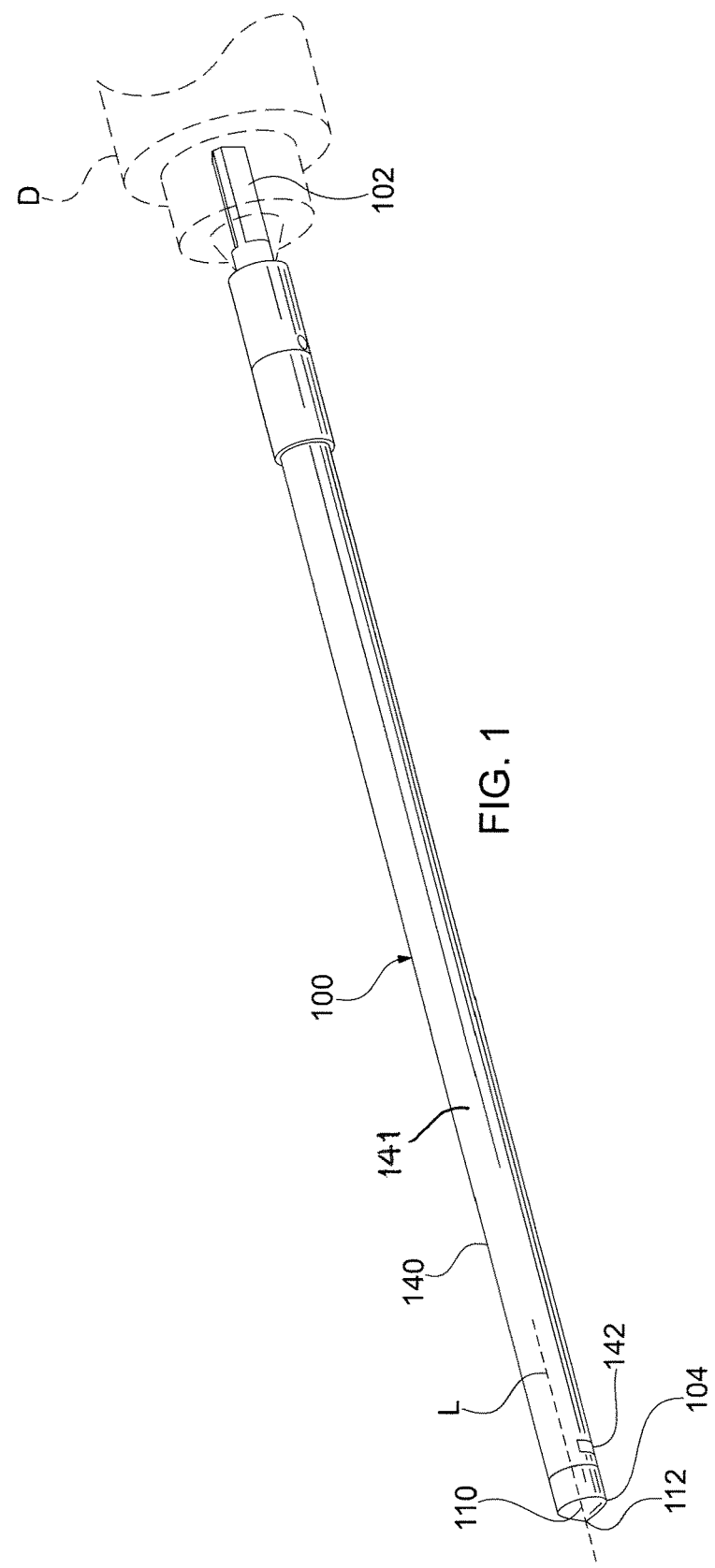
FIG. 1 is a perspective view of a bone tunneling instrument in accordance with one embodiment of the invention.
Figure 2:
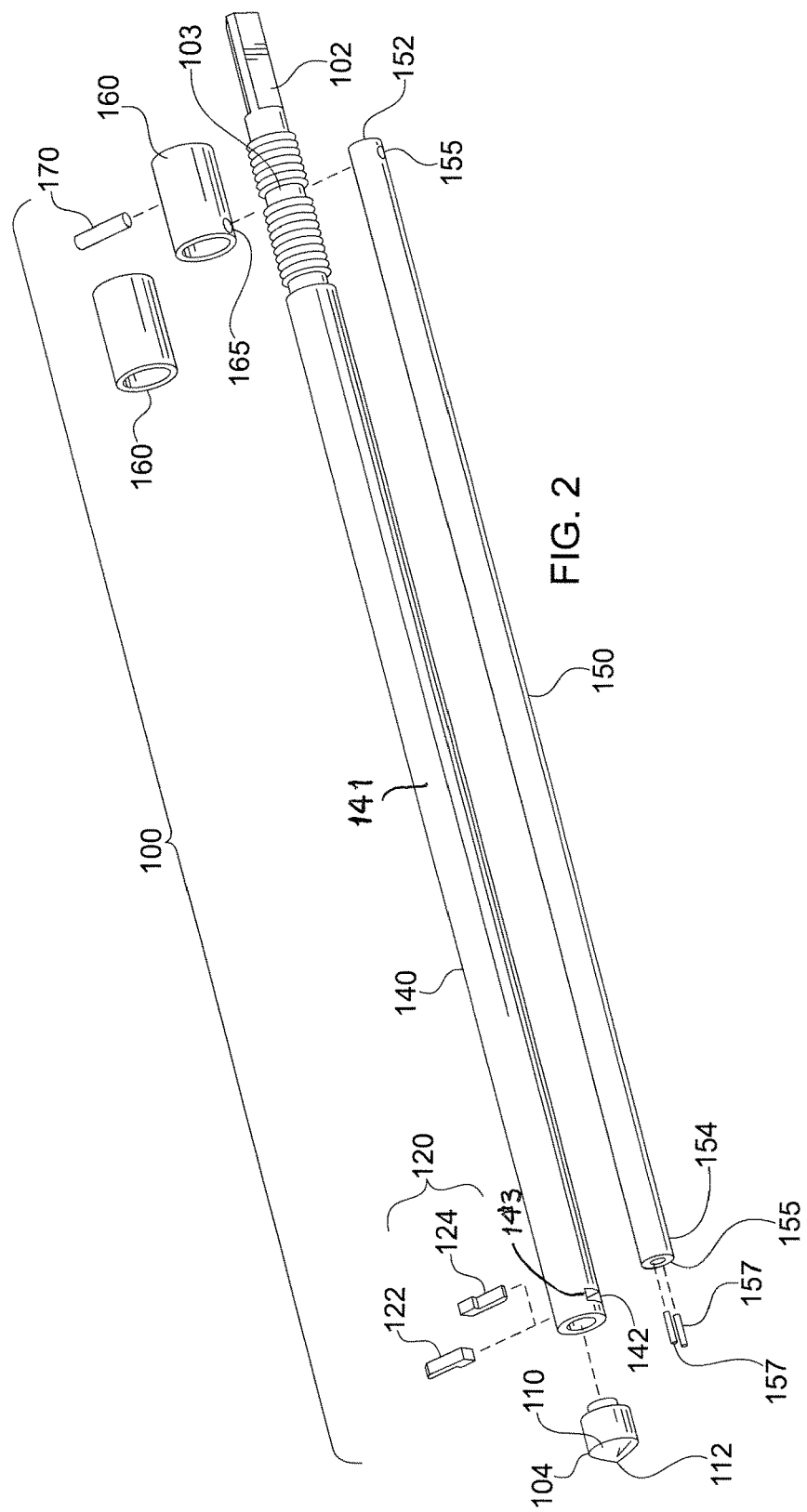
FIG. 2 is an exploded perspective view of the bone tunneling instrument of FIG. 1.

Referring to FIGS. 1 and 2, an instrument in the form of a intraosseous tunneling reamer 100 is shown in accordance with a first embodiment of the invention. Reamer 100 is an instrument that can form a tunnel or socket in bone that has a constant cross sectional area. Reamer 100 can also form a tunnel or socket in bone that has one or more cross sectional areas that vary at different sections along the length of the tunnel.

Reamer 100 has a proximal end 102, a distal end 104 and a sharpened end 110 at the distal end. Sharpened end 110 has a sharp piercing tip 112 that is solid or non-cannulated. Reamers in accordance with the invention can feature a solid sharpened piercing tip like sharp piercing tip 112. Alternatively, reamers in accordance with the invention can feature a blunt tip, a hollow tip, or a drill bit. Regardless of the configuration, reamers in accordance with the invention are designed to create a small diameter tunnel in bone. The tunnel can be formed by punching or driving the distal end of the reamer through cortical bone and into cancellous bone.

Reamers in accordance with the invention also include a cutting element for cutting one or more enlarged sections in a tunnel during or after formation of the tunnel. The cutting element can be deployed with an expansion element that is operable to expand the cutting element radially outwardly with respect to a longitudinal axis L of the reamer. Once the cutting element is radially expanded, the cutting element can be rotated to cut a larger diameter section in the tunnel. A surgical drill, driver or other source of torque can be attached to proximal end 102 of reamer 100 to rotate the cutting element to cut the enlarged section in the tunnel. In this regard, proximal end 102 can include beveled or flattened sections that allow a drill, driver or other tool to be clamped to the reamer 100 using a chuck or other known attachment mechanism. FIG. 1 schematically shows the chuck of a drill D clamped around the proximal end 102 of reamer 100.

Cutting elements in accordance with the invention can take various forms, including but not limited to one or more teeth, spikes, burrs, blades or blade sections that project radially outwardly from the reamer. For example, reamer 100 features a cutting element 120 that is provided in the form of one or more blades, and more specifically, two opposing blades comprised of a first blade 122 and a second blade 124. Blades in accordance with the invention can have cutting faces with a number of possible geometries for cutting bone.

Referring to FIG. 3, blade 122 includes a first end 122a having a cutting face 122b, and a second end 122c. The outer perimeter length of first end 122a is longer than the outer perimeter length of second end 122c. First and second ends 122a and 122c are convexly curved. Cutting face 122b has a cutting edge 128 that can cut radially outwardly in bone, as well as in an axial direction in bone, i.e. in the lengthwise direction in a tunnel. The convex curvatures of first and second ends 122a and 122c each have one uniform or constant radius of curvature, and follow an arc having a uniform or constant circular curvature. It will be understood that blade ends in accordance with the invention can also follow a curve having a non-uniform or compound curvature with multiple radii of curvature. In embodiments with cylindrical housings, such as the housing to be described, the first and second ends of the blade preferably follow a circular curvature, so that when the blade is fully retracted into the housing, the first and second ends of the blade sit flush with, and conform to the same circular curvature of, the cylindrical housing. In the flush arrangement, the exterior surfaces of the first and second ends form a smooth and continuous surface with the exterior of the cylindrical housing, with no discontinuity, projection, or indentation.

Blade 124 also includes a first end 124a having a cutting face 124b, and a second end 124c. The outer perimeter length of first end 124a is longer than the outer perimeter length of second end 124c. First end 124a and second end 124c are convexly curved. Cutting face 124b features a cutting edge 128 that can cut radially outwardly as well as in an axial direction. The convex curvatures of first and second ends 124a and 124c each have one radius of curvature, as described with first and second ends 122a and 122c.

Cutting face 122b of first blade 122 is positioned adjacent to second end 124c of second blade 124. Similarly, cutting face 124b of second blade 124 is positioned adjacent to second end 122c of first blade 122. In this arrangement, cutting face 122b and second end 124c follow a common arc or curve 127. Likewise, cutting face 124b and second end 122c follow a common arc or curve 129. In the embodiment shown, the cutting faces 122b and 124b, and the second ends 122c and 124c, are all circular with a constant radius originating from longitudinal axis L of the instrument. As such, arcs 127 and 129 coincide with a circular outline C. Cutting faces 122b and 124b, and second ends 122c and 124c, all confirm to circular outline C when first and second blades 122 and 124 are in the fully retracted state. In the fully assembled state, expansion of the first and second blades 122 and 124 radially outwardly causes the blades to expand in opposite directions relative to one another. In the expanded or deployed position, cutting face 122b and second end 124c are offset and no longer on the same curve, and cutting face 124b and second end 122c are offset and no longer on the same curve.

The distal ends of instruments in accordance with the invention have a first cross sectional area that corresponds to the cross sectional area of the tunnel to be formed. The distal ends can have a circular cross section or a non-circular cross section. In this description, cross sections of the tunnel may at times be described as having certain "diameters". Nevertheless, it will be understood that tunnels formed by instruments in accordance with the invention can form circular or non-circular cross sections, as for example in cases where a non-circular piercing tip and shaft are tapped into the bone.

Cutting elements in accordance with the invention define a second cross sectional area on the instrument when partially or fully expanded. The second cross sectional area is wider than the first cross sectional area, so that when the cutting elements are rotated in a tunnel formed by the sharpened end, the cutting elements carve out a void, counterbore or space that circumferentially surrounds the tunnel. The carved out area is larger in cross section than the cross section of the adjoining section(s) of the tunnel that are not cut by the cutting element.

Enlarged sections of tunnel can be used as sockets for allograft transplantation, PCL reconstruction, ACL reconstruction, and other procedures. When instrument 100 creates a socket, the socket will have a radius that corresponds to a cutting path P defined by cutting faces 122b and 124b, as shown in FIG. 5. Cutting path P has a diameter that is larger than the radius of an adjoining section of the tunnel that is not cut by the cutting element. The dimensions of the tunnel and socket can be selected based on numerous factors, including but not limited to whether a bone anchor or implant is being implanted and/or the type of bone anchor or implant being implanted.

For example, the maximum diameter of the sharpened tip can be between about 4.75 mm and about 5.25 mm. A preferable maximum diameter of the sharpened tip might be about 5.0 mm. The maximum diameter of cutting path P (i.e. the circular outline C that coincides with cutting faces 122b and 124b when the cutting blades are fully expanded) can be between about 6.75 mm and about 7.25 mm. A preferable maximum diameter of cutting path P can be about 7.0 mm. Other diameters outside of these ranges are also contemplated in accordance with the invention, and can work equally well to form tunnels and expanded sections of different sizes.

The cutting element can be integrated with the reamer in various ways in accordance with the invention. For example, reamers in accordance with the invention can include hollow tubes or cylinders in which the cutting element is housed. The tubes or cylinders can include one or more apertures. Reamer 100 includes a cylindrical hollow shaft or containment tube 140 having a sidewall 141. Sidewall 141 defines two diametrically opposed apertures 142. That is, the two apertures 142 are separated from one another by an angle of 180 degrees along the circumference of shaft 140. Each aperture 142 is located proximally to the distal end of the shaft 140, and is bordered by four sides 143. The four sides 143 of each aperture 142 are closed within sidewall 141 of shaft 140, so that the aperture itself is enclosed. It will be understood, that apertures in accordance with the invention can also be closed on three sides, and open on a fourth side, such as where each aperture borders the end of a cylinder. However, it is preferable in many instances to use closed apertures and have a closed end on the distal end of the shaft to avoid openings that can become clogged with bone fragments.

Each aperture 142 is axially and radially aligned with a first end (and cutting face) of one blade and a second end of the other blade, as shown. In the fully assembled state, cutting faces 122b and 124b, and second ends 122c and 124c, are disposed within hollow shaft 140 in a non-deployed state, as shown in FIG. 4. Preferably, cutting faces 122b and 124b, and second ends 122c and 124c, are positioned flush with the outer perimeter of containment tube 140, forming a smooth and continuous exterior surface as previously described. In a deployed state, cutting faces 122b and 124b project through the apertures 142 to a position outside the outer perimeter of containment tube 140, while second ends 122c and 124c are retracted inside the outer perimeter of containment tube, as shown in FIG. 5.

Blades in accordance with the invention can be expanded and retracted using a variety of mechanisms. Reamer 100 features an expansion element in the form of an activation rod 150 that is at least partially housed inside and rotatable within containment tube 140. Activation rod 150, also referred to as an activation pin, includes a proximal end 152 and a distal end 154 having a distal end face 155. Cutting blades 122 and 124 are each pivotably and slidably coupled to distal end face 155 with a pin 157. Each cutting blade 122 and 124 defines an elongated slot 159 that fits over one of the pins 157 to mount the cutting blade to distal end face 155. Pins 157 work as a cam mechanism to expand and retract cutting blades 122 and 124 when activation rod 150 is rotated.

To displace cutting blades 122 and 124 radially outwardly to the expanded position, activation rod 150 is rotated inside tube 140 through a small angle, for example an angle of 30 degrees about the longitudinal axis L. As activation rod 150 is rotated, the distal end face 155 also rotates. The outer ends of blades 122 and 124 are captively guided inside the opposing apertures 142, which limits the path of motion of the blades during this rotation. One or more walls in each aperture 142 controls the orientation and trajectory of its respective blade throughout expansion and retraction. Movement of each blade 122 and 124 is also limited and controlled by the blade's sliding engagement with one of the pins at the blade's midsection. During expansion, the blades 122 and 124 move in opposite directions and apart from one another through sidewall 141. During retraction, the blades move in opposite directions and toward one another through sidewall 141.

Activation rods in accordance with the invention can be rotated using various mechanisms. In reamer 100, an activation sleeve or thimble activator 160 is used to rotate activation rod 150. Sleeve 160 is connected to activation rod 150 by a dowel pin 170. Dowel pin 170 is secured into a bore 165 in sleeve 160 and into a bore 155 in activation rod 150 by press fitting or other means. Dowel pin 170 extends through an elongated slot 103 that extends through the wall of containment tube 140. Slot 103 is elongated in a circumferential or peripheral direction with respect to the containment tube's circumference to allow dowel pin 170, and consequently sleeve 160 and activation rod 150, to rotate through a limited range of motion in a radial direction relative to containment tube 140. To expand blades 122 and 124, sleeve 160 can be rotated in a first direction, e.g. clockwise, over containment tube 140 to rotate activation rod 150 and displace blades 122 and 124 radially outwardly. To retract blades 122 and 124, sleeve 160 can be moved in a second direction over containment tube 140, opposite the first direction, e.g. counterclockwise, to displace blades 122 and 124 radially inwardly.

Figure 6:
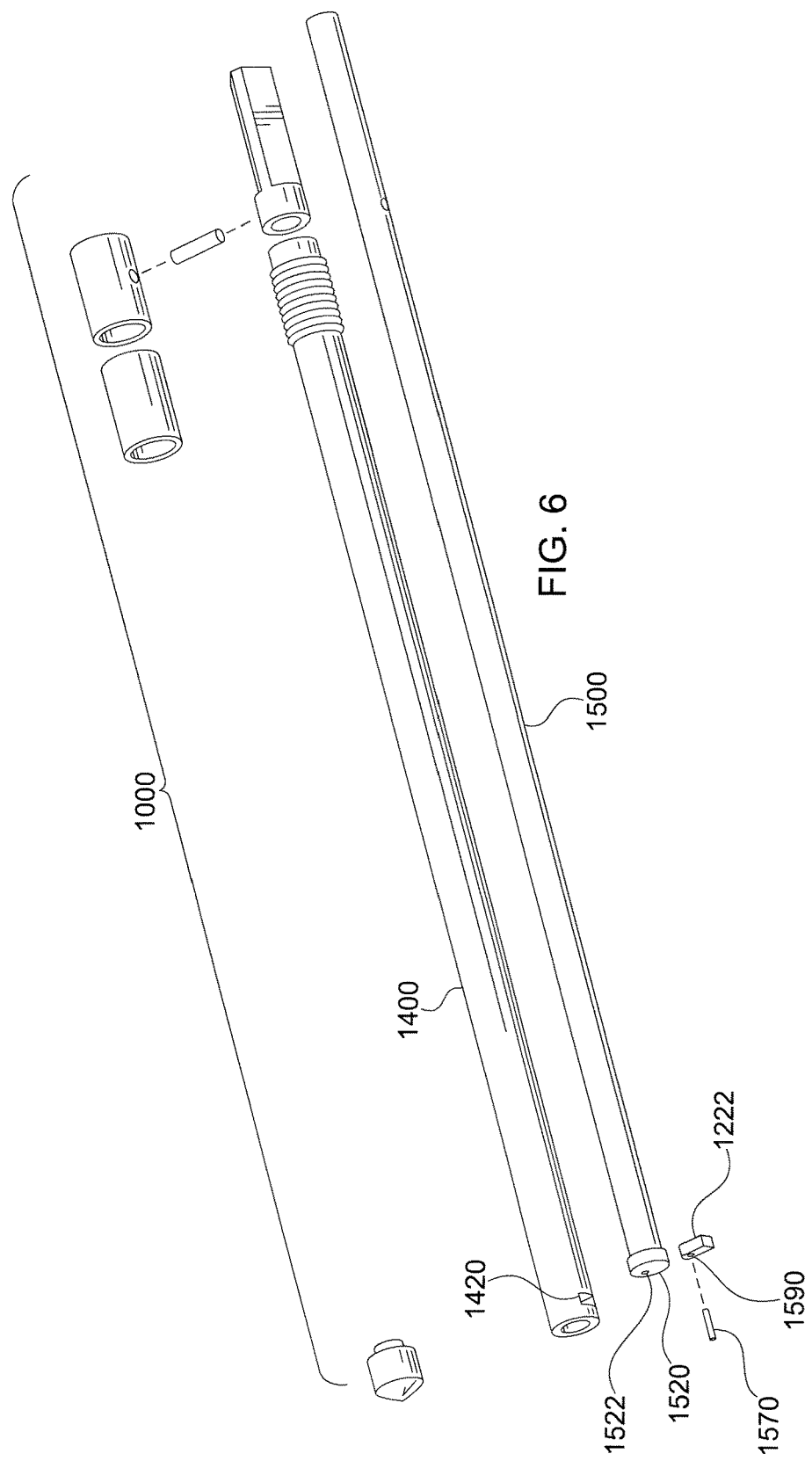
FIG. 6 is an exploded perspective view of another bone tunneling instrument in accordance with the invention.

Referring to FIG. 6, an alternate reamer 1000 is shown in accordance with another embodiment of the invention. Reamer 1000 is identical to reamer 100 in many respects. For brevity, features in reamer 1000 that differ from those in reamer 100 will be described, with the understanding that other features not described in reamer 1000 can be similar or identical to those in reamer 100.

Reamer 1000 features only one blade 1222 for cutting enlarged diameter sections in a bone tunnel. Blade 1222 is mountable to a circular disk 1520 at a distal end of an activation rod 1500 as shown. Activation rod 1500 is rotatable inside a hollow containment tube 1400. Disk 1520 has a bore 1522 that is positioned off center with respect to the center of the disk. Blade 1222 has an opening 1590, which can be similar or identical to elongated slots 159, or alternatively, a circular hole. Opening 1590 is adapted to fit over a pin 1570 that is welded or otherwise mounted in bore 1522. Blade 1222 can be expanded radially outwardly through an aperture 1420 in containment tube 1400 to extend beyond the outer perimeter of the containment tube by rotating activation rod 1500 in a first direction. Similarly, blade 1222 can be retracted radially inwardly through aperture 1420 until it is fully contained inside containment tube 1400, by rotating activation rod 1500 in a second direction opposite the first direction, the manner of operation being similar or identical to the operation of reamer 100.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An instrument for cutting bone, the instrument having a longitudinal axis and comprising:
    a hollow shaft comprising a sidewall;
    a cutting element at least partially housed in the hollow shaft, the cutting element comprising one or more cutting blades that are radially expandable, relative to the longitudinal axis, through the sidewall;
    a piercing tip on a distal end of the hollow shaft, the piercing tip located distally of the one or more cutting blades; and
    an expansion element for radially expanding the one or more cutting blades radially outwardly with respect to the longitudinal axis of the instrument and through the sidewall of the hollow shaft,
    each of the one or more cutting blades comprising a first end having a cutting edge, a second end opposite the first end, and a center point located equidistant from the first end and the second end,
    wherein the expansion element comprises an activation rod disposed inside the hollow shaft, and
    wherein each of the one or more cutting blades is mounted to the activation rod at its center point.

2. The instrument of claim 1, wherein the sidewall of the hollow shaft defines one or more apertures extending completely through the sidewall.

3. The instrument of claim 2, wherein the one or more apertures are axially and radially aligned with the one or more cutting blades inside the hollow shaft.

4. The instrument of claim 2, wherein each of the one or more apertures are closed on four sides within the sidewall of the hollow shaft.

5. The instrument of claim 1, wherein the activation rod comprises a distal end, the distal end having a distal end face.

6. The instrument of claim 5, wherein the one or more cutting blades are mounted to the distal end face.

7. The instrument of claim 6, wherein the one or more cutting blades are slidably coupled to the distal end face.

8. The instrument of claim 5, wherein the one or more cutting blades are radially expandable, relative to the longitudinal axis, through the sidewall in response to rotation of the activation rod inside the hollow shaft.

9. The instrument of claim 1, wherein the activation rod is rotatable relative to the hollow shaft between a first orientation, in which the one or more cutting blades are radially expanded through the one or more apertures to a cutting position, and a second orientation, in which the one or more cutting blades are radially retracted through the one or more apertures to a stowed position.

10. The instrument of claim 9, wherein the one or more cutting blades define a circular cutting path in the cutting position, the circular cutting path having a cutting path diameter larger than a diameter of the hollow shaft.

11. The instrument of claim 10, wherein the cutting path diameter is between about 6.75 mm and about 7.25 mm.

12. The instrument of claim 10, wherein the cutting path diameter is about 7.0 mm.

13. The instrument of claim 1, wherein the one or more cutting blades are coupled to a distal end of the activation rod.

14. The instrument of claim 13, wherein the one or more cutting blades are pivotably mounted to the distal end of the activation rod.

15. The instrument of claim 13, wherein the one or more cutting blades are slidably coupled to the distal end of the activation rod.

16. The instrument of claim 13, wherein the activation rod comprises a cam mechanism for radially expanding the one or more cutting blades.

17. The instrument of claim 16, wherein the cam mechanism comprises one or more pins extending longitudinally from the distal end of the activation rod.

18. The instrument of claim 17, wherein the one or more cutting blades are mounted on the one or more pins to mount the one or more cutting blades to the distal end of the activation rod.

19. The instrument of claim 1, wherein the piercing tip comprises a drill bit.

20. The instrument of claim 1, wherein the one or more cutting blades are entirely contained within a perimeter of the hollow shaft when the activation rod is rotated to the second orientation.

21. The instrument of claim 1, wherein the first end and second end of each of the one or more cutting blades are convexly curved.

22. The instrument of claim 21, wherein the first end and second end of each of the one or more cutting blades are circular.

23. The instrument of claim 22, wherein the first end and second end of each of the one or more cutting blades have a common radius of curvature, and the hollow shaft is cylindrical with a circular exterior sharing said common radius of curvature, such that the one or more cutting blades are retractable into the hollow shaft with their respective first end and second end sitting flush with, and conforming to, the circular exterior of the hollow shaft to form a smooth and continuous exterior.

24. The instrument of claim 1, wherein the first end of each of the one or more cutting blades comprises a first perimeter length, and the second end of each of the one or more cutting blades comprises a second perimeter length, the first perimeter length being longer than the second perimeter length.

25. An instrument for cutting bone, the instrument having a longitudinal axis and comprising:
    a hollow shaft comprising a sidewall;
    a cutting element at least partially housed in the hollow shaft, the cutting element comprising one or more cutting blades that are radially expandable, relative to the longitudinal axis, through the sidewall;

a piercing tip on a distal end of the hollow shaft, the piercing tip located distally of the one or more cutting blades; and an expansion element for radially expanding the one or more cutting blades radially outwardly with respect to the longitudinal axis of the instrument and through the sidewall of the hollow shaft, wherein the expansion element comprises an activation rod disposed inside the hollow shaft, wherein the activation rod is rotatable relative to the hollow shaft between a first orientation, in which the one or more cutting blades are radially expanded through one or more apertures to a cutting position, and a second orientation, in which the one or more cutting blades are radially retracted through the one or more apertures to a stowed position, each of the one or more cutting blades comprising a first end having a cutting edge, a second end opposite the first end, and a center point located equidistant from the first end and the second end, wherein each of the one or more cutting blades is mounted to the activation rod at its center point, and wherein the one or more cutting blades are entirely contained within a perimeter of the hollow shaft when the activation rod is rotated to the second orientation.

* * * * *